(12) United States Patent
Morikawa et al.

(10) Patent No.: US 6,525,807 B1
(45) Date of Patent: Feb. 25, 2003

(54) PARTICLE ANALYZING APPARATUS

(75) Inventors: Takashi Morikawa, Kakogawa (JP);
Hiroyuki Inoue, Kakogawa (JP);
Kimiyo Kubo, Kakogawa (JP); Yoshiro Ikeuchi, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/488,538

(22) Filed: Jan. 21, 2000

(30) Foreign Application Priority Data

Jan. 21, 1999 (JP) .......................................... 11-013657
Dec. 28, 1999 (JP) .......................................... 11-374377

(51) Int. Cl.[7] ........................ G01N 21/00; G01N 15/02; G01N 21/86
(52) U.S. Cl. ........................ 356/72; 356/336; 356/338; 250/559.4
(58) Field of Search ........................... 356/72, 39, 335, 356/336, 338, 73; 250/461.2, 462.1, 483.1, 484.2, 559.4, 559.41, 559.44; 600/309, 310, 322, 317, 345, 308

(56) References Cited

U.S. PATENT DOCUMENTS 5,125,737 A * 6/1992 Rodriguez et al. .......... 356/338
5,631,165 A   5/1997 Chupp et al.
5,656,499 A   8/1997 Chupp et al.
5,731,867 A   3/1998 Katayama
5,824,269 A  10/1998 Kosaka et al.

FOREIGN PATENT DOCUMENTS

JP      9508705 T    9/1997

* cited by examiner

Primary Examiner—Richard A. Rosenberger
Assistant Examiner—Gordon Stock
(74) Attorney, Agent, or Firm—Birch, Stewart, Kolasch & Birch, LLP

(57) ABSTRACT

A particle analyzing apparatus outputs a measurement result with high reliability with respect to a measurement item. The particle analyzing apparatus includes a measuring part, a judgement processing part, and an output part. The measuring part includes a fluid part, a control part, a first measuring part, a second measuring part, a hystogram preparing part, and a scattergram preparing part. The fluid part sucks up a blood sample in a test tube by a pipette. The control part controls the fluid part, the first measuring part, and the second measuring part. Measurement data measured by the first measuring part and the second measuring part are sent to the judgement processing part, and after judgement is made in the judgement processing part, a measurement result is outputted by the output part. The first measuring part makes measurement on the basis of an impedance system, and the second measuring part makes measurement on the basis of a flow cytometory system.

10 Claims, 13 Drawing Sheets

PARTICLE ANALYZING APPARATUS

CROSS-REFERENCES TO RELATED APPLICATIONS

This application is related to Japanese patent applications No. HEI 11(1999)-013657 filed on Jan. 21, 1999 and No. HEI 11(1999)-374377 filed on Dec. 28, 1999 whose priorities are claimed under 35 USC §119, the disclosure of which are incorporated herein by reference in its entirety.

BACKGROUND OF THE INVENTION

1. Field of the Invention

The present invention relates to a particle analyzing apparatus for measuring a measurement item of a particle to be analyzed by means of a plurality of measuring parts with different measurement principles.

2. Description of the Related Art

In a particle analyzing apparatus, it is general that measurement is made for a measurement item on the basis of a measurement principle, and its measurement result is displayed. However, in a sample inspection, since samples include both a normal sample and an abnormal sample, it is not necessarily possible to obtain a highly reliable measurement result by a measurement principle. For example, in measurement of the count of platelets, there is no measurement principle capable of providing an accurate measurement result for any samples, and each measurement principle has its merits and demerits.

As systems for individually detecting the count of platelets, there are an electrical detection system and an optical detection system. In an impedance system as a system of the former, electrodes are arranged at both sides of an aperture, and an impedance change generated when a blood cell in an aqueous suspension passes through the aperture is detected. When the blood cell passes through the aperture, a pulse signal in propart to the volume of the blood cell is obtained, and by performing data processing of this pulse signal, the count of platelets and the volume of the platelet can be obtained. In this system, although the platelet is differentiated from an erythrocyte on the basis of its size, where there are fragment erythrocytes, micro erythrocytes, or giant platelets, there is a case where the accurate count of the platelets can not be obtained.

In a flow cytometory system as a system of the latter, scattered light and fluorescence generated when a blood cell in the aqueous suspension passes through an irradiation area of a laser beam is detected by an optical detector. It is possible to obtain a two-dimensional distribution of the detected scattered light and fluorescence. By analyzing this distribution, differentiation of the platelets can be made with high accuracy. That is, distinction from the fragment erythrocytes or the micro erythrocytes becomes easy, and even in the case where there are giant platelets, the count of platelets can be measured. However, since a staining solution is used, there is a sample in which nonspecific staining by the staining solution can be seen, and there is also a case where the count of platelets can not be accurately measured.

There is devised an automatic analyzing apparatus in which measurement of the count of platelets can be made through two systems of the impedance system and the flow cytometory system (Japanese Patent Unexamined Publication No. Hei. 9-508705). According to the apparatus, the count of platelets measured through the flow cytometory system is reported as patient data, and the count of platelets measured through the impedance system is used as a diagnostic tool for monitoring the performance of the apparatus. However, there is no disclosure that comparison is made between the accuracy of platelet measurement based on a measurement principle and that based on another measurement principle, and that the count of platelets having high reliability is provided.

SUMMARY OF THE INVENTION

The present invention has been made in view of the foregoing circumstances, and an object of the invention is to provide a particle analyzing apparatus capable of outputting a measurement result with high reliability.

The term "reliability" as referred to in the specification and apended claims means an index for quantitatively reflecting reliance on a certain item.

According to the present invention, there is provided a particle analyzing apparatus comprising a measuring part capable of measuring a specific measurement item of a particle to be analyzed with at least two measurement principles; a judgement processing part for calculating reliability as to at least one measurement principle based on a measurement result in the measuring part and for performing judgement processing of the measurement result in the measuring part based on the calculated reliability; and an output part for outputting the measurement item based on the at least one reliability judged in the judgement processing part.

Here, the at least two measurement principles, for example, include a first measurement principle and a second measurement principle, the first measurement principle is based on an electrical detection system for detecting an electrical change generated when the particle passes through its detection zone, and the second measurement principle is based on an optical detection system for detecting an optical change generated when the particle passes through its detection zone.

The measuring part may be made of one part, or may be made of a plurality of parts. Although the measuring part can measure the specific measurement item of the particle to be analyzed with the at least two measurement principles, only one measurement principle may be actually used.

The judgement processing part may calculate a plurality of reliabilities or may calculates one reliability. Besides, the judgement processing part may set an area which is adjacent to a distribution area of particles to be analyzed in a distribution diagram obtained as a result of measurement in the measuring part and in which any particle does not normally appear. The reliability in this case is, for example, a frequency of appearance of the particles in the area.

The output part may output the measurement item based on a higher (in the case of two) or the highest (in the case of three or more) reliability among the plurality of reliabilities in the judgement processing part, or may output the measurement item based on one reliability in the judgement processing part and may output a definite message or the like.

In the electrical detecting system, it is possible to use an electrical resistance system (impedance system) to detect a resistance change (impedance change) generated when a particle in the aqueous suspension passes through an aperture between two electrodes. As the optical detecting system, it is possible to use a flow cytometory system.

The judgement processing part can be structured by a microcomputer composed of a CPU, ROM, RAM and I/O port, or a personal computer. As the output part, a display device such as a CRT or a liquid crystal display, or a printing device such as a printer can be used.

The particle to be analyzed is, for example, a blood cell component particle such as a platelet, leukocyte, or erythrocyte, a cell in urine, a cultured cell, or a microorganism. The measurement item is, for example, an item as to the count or volume of blood cell component particles such as platelets, leukocytes, or erythrocytes, or an item as to the count or volume of cells in urine, cultured cells, microorganisms, or the like.

DETAILED DESCRIPTION OF THE PREFERRED EMBODIMENTS

Figure 1:
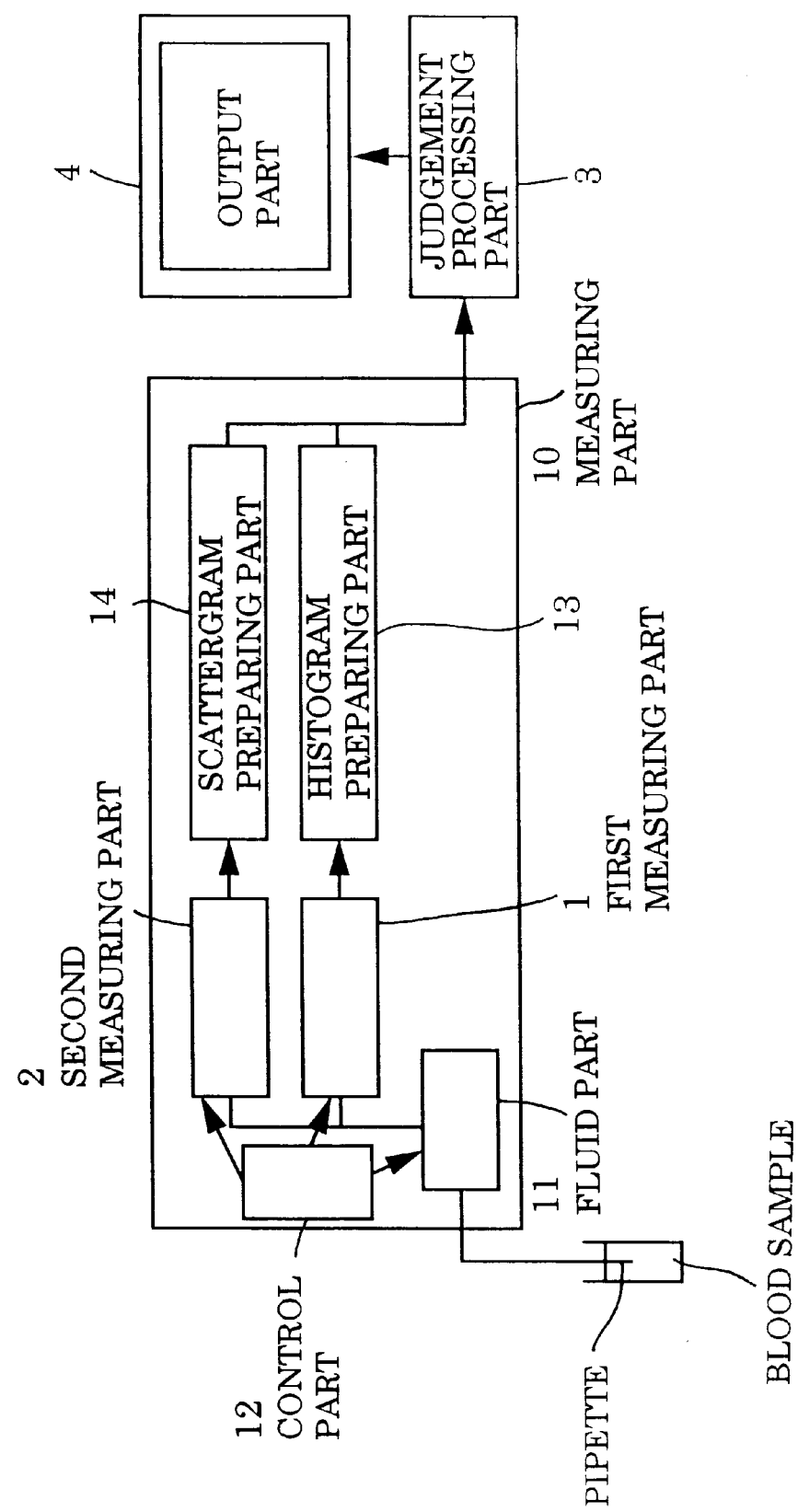
FIG. 1 is a block diagram showing an embodiment of the present invention.

Preferred embodiments of the present invention will be described with reference to the drawings. FIG. 1 is a block diagram of the present invention. In FIG. 1, a particle analyzing apparatus is constituted by a measuring part 10, a judgement processing part 3, and an output part 4. The measuring part 10 is constituted by a fluid part 11, a control part 12, a first measuring part 1, a second measuring part 2, a histogram preparing part 13, and a scattergram preparing part 14. The fluid part 11 sucks up a blood sample in a test tube by means of a pipette. The control part 12 controls the fluid part 11, the first measuring part 1, and the second measuring part 2. The measurement data, measured by the first measuring part 1 and the second measuring part 2, are sent to the judgement processing part 3, and after judgement is made by the judgement processing part 3, a measurement result is outputted by the output part 4. Here, the first measuring part 1 makes measurement through an electrical resistance system, and the second measuring part 2 makes measurement through a flow cytometry system.

Figure 11:
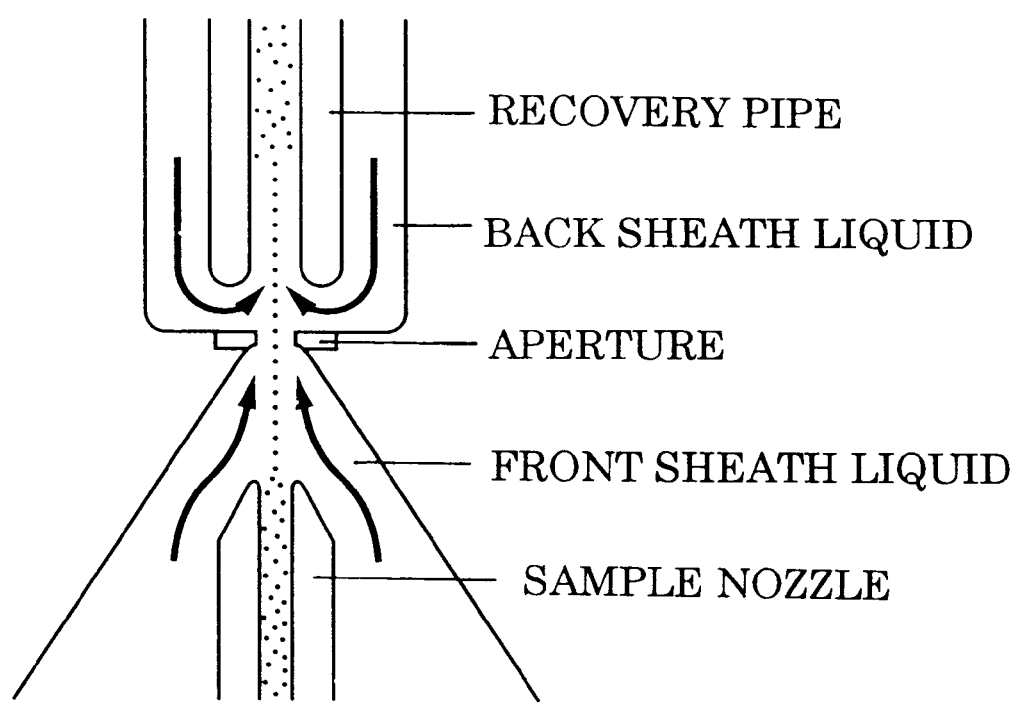
FIG. 11 is a sectional diagram showing a first measuring part of the embodiment of the present invention.

FIG. 11 is a sectional diagram of a detecting part of the first measuring part 1. A sample nozzle is disposed at an upstream side of an aperture, and although not shown, electrodes are disposed at an upstream side and a downstream side of the aperture, that is, at a sample nozzle side and a recovery pipe side, and a DC current flows between the electrodes. A DC resistance between the electrodes is changed when a blood cell passes through the aperture.

The blood cell discharged from the sample nozzle is enclosed in a front sheath liquid and passes through the center part of the aperture. After passing through the aperture, the blood cell is enclosed in a back sheath liquid, and is sent into a recovery pipe.

Next, steps up to calculation of the count of platelets from a blood sample will be described. Blood of 4.8 µl, together with CELLPACK™ diluent (made by SYSMEX CORPORATION.) of 2 ml, is transferred to a diluting chamber, and is diluted. The prepared diluted sample is discharged from the sample nozzle by a quantitative syringe, a change in DC resistance is taken out as a pulse signal, and particle size distribution diagrams are prepared based on the signal (FIGS. 3B, 5B, 7B, and 9B). In these particle size distribution diagrams, a division line (b) between the platelets and noises, and a division line (c) between the platelets and erythrocytes are drawn, only the platelet part (between the lines (b) and (c)) is differentiated, and the count of platelets is calculated.

Figure 12:
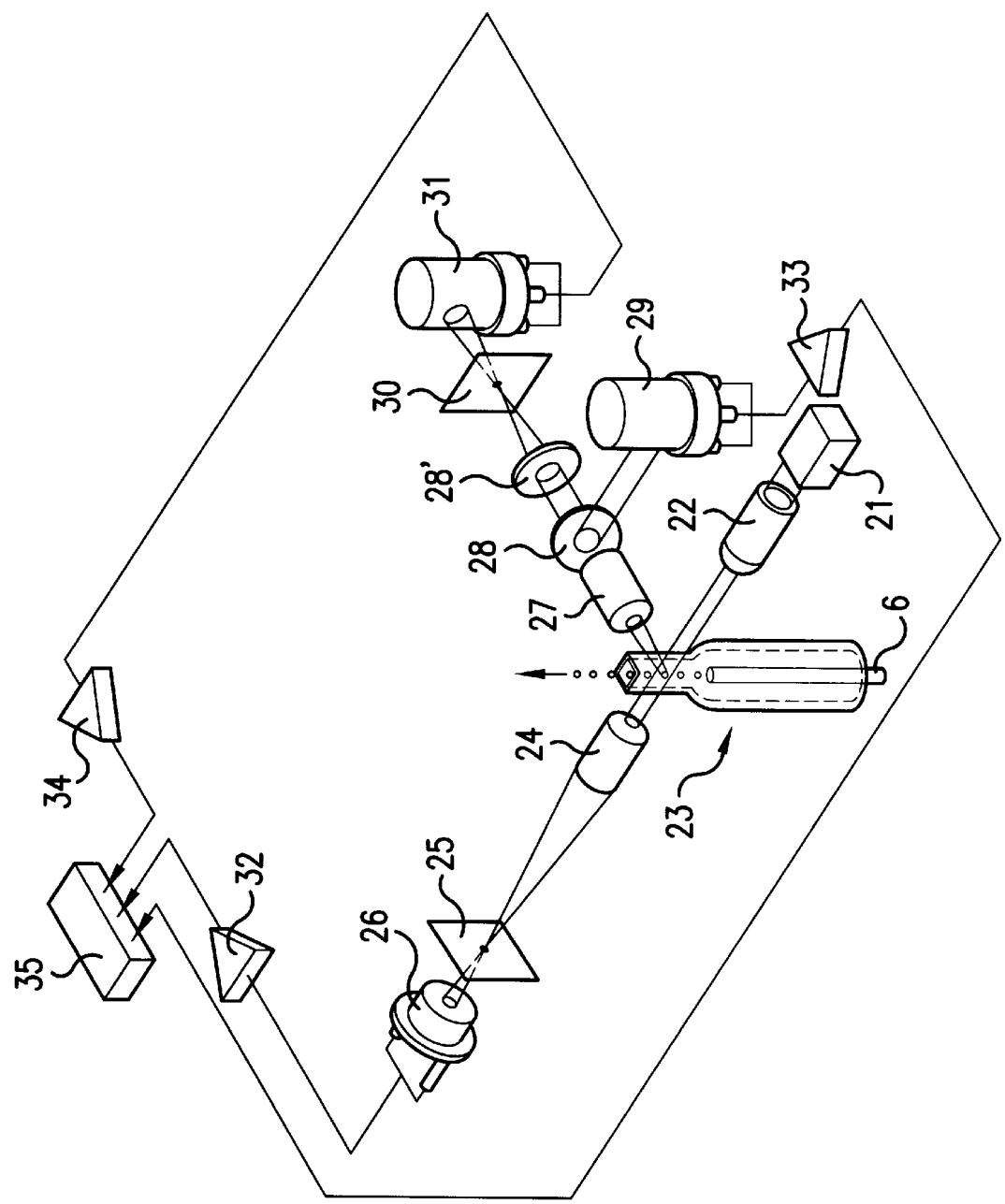
FIG. 12 is a perspective diagram showing a second measuring part of the embodiment of the present invention.

FIG. 12 is a perspective diagram showing an optical system of the second measuring part 2. In the drawing, a beam radiated from a laser diode 21 irradiates an orifice part of a sheath flow cell 23 through a collimate lens 22. Forward scattered light emitted from a blood cell passing through the orifice part is incident on a photodiode 26 through a condensing lens 24 and a pinhole plate 25.

On the other hand, with respect to side scattered light and side fluorescence emitted from the blood cell passing through the orifice part, the side scattered light is incident on a photomultiplier tube (hereinafter referred to as a photomul) 29 through a condensing lens 27 and a dichroic mirror 28, and the side fluorescence is incident on a photomul 31 through the condensing lens 27, the dichroic mirror 28, a filter 28', and a pinhole plate 30.

A forward scattered light signal outputted from the photodiode 26, a side scattered light signal outputted from the photomul 29, and a side fluorescence signal outputted from the photomul 31 are respectively amplified by amplifiers 32, 33, and 34, and are inputted to an analyzing part 35.

Next, steps up to calculation of the count of platelets from the blood sample will be described. Blood of 4.5 µl is added with RET-SEARCH (II)™ staining solution (made by SYSMEX CORPORATION.) of 18 µl. By causing a reaction to occur for 31 seconds in this state, reticulocytes and the like are stained. This treated sample is discharged from the nozzle 6 by the quantitative syringe. FIGS. 4B, 6B, 8B, and 10B show examples in which among information obtained by the optical measurement, the side fluorescence and the forward scattered light are converted into scattergrams. The platelets are differentiated from noises, mature erythrocytes, and reticulocytes, and the count of platelets is calculated.

Figure 2:
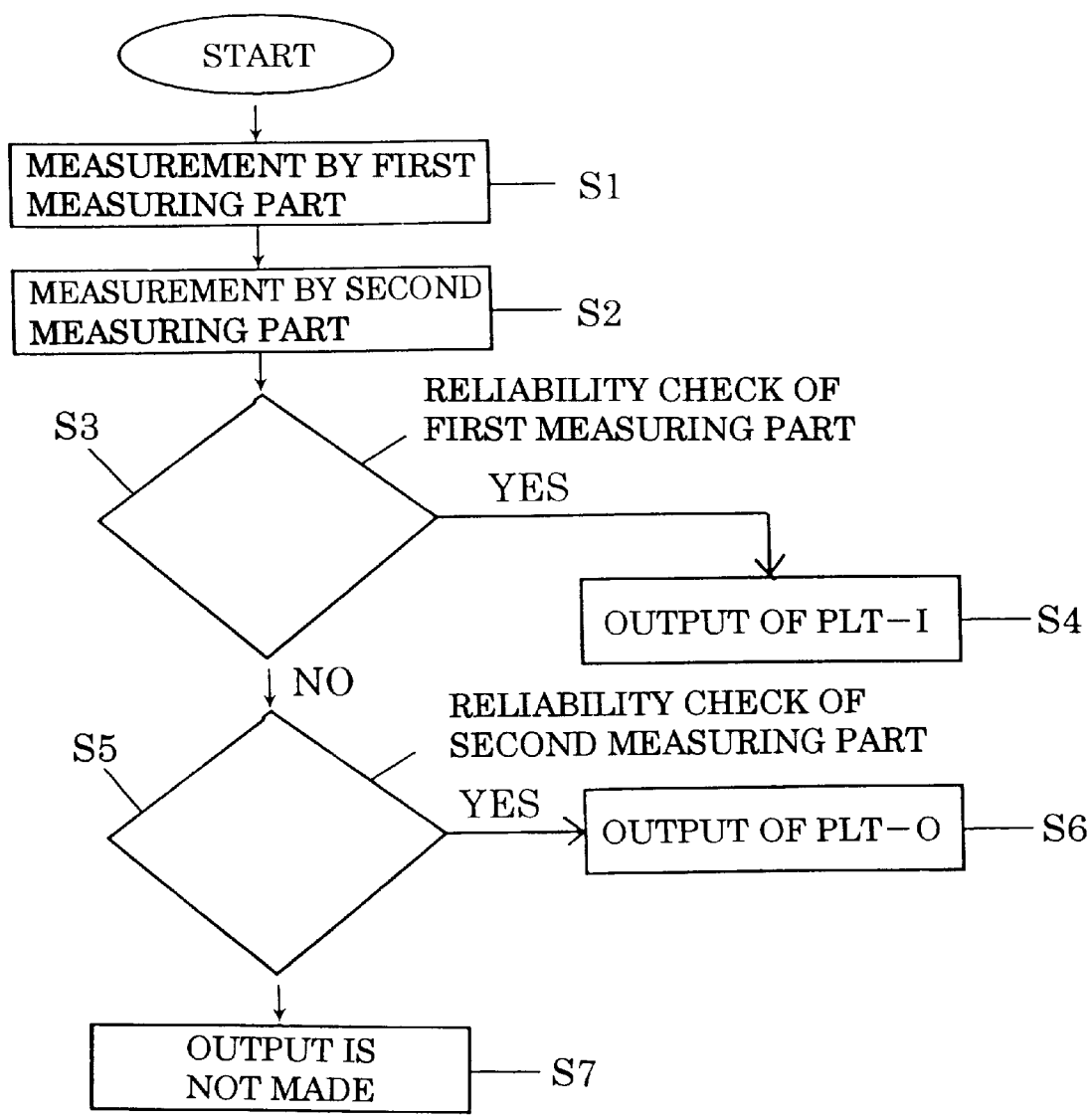
FIG. 2 is a measurement flowchart of the embodiment of the present invention.

Next, on the basis of a flowchart shown in FIG. 2, a description will be made on a procedure up to a stage in which measurement of the count of platelets is made with a plurality of different measurement principles and a measurement result with high reliability is outputted.

First, measurement by the first measuring part and measurement by the second measuring part are carried out (steps S1 and S2), and reliability of PLT-I is checked (step S3). In the case where the reliability is higher than a fixed value, the measurement result of PLT-I is outputted (step S4). In the case where the reliability of PLT-I is lower than the fixed value, reliability of PLT-O is checked (step S5). In the case where the reliability is higher than a fixed value, the measurement result of PLT-O is outputted (step S6). In the case where the reliability of PLT-O is lower than the fixed value, either measurement result is not outputted (step S7).

Here, PLT-I indicates the count of platelets obtained by measurement in the first measuring part 1, and PLT-O indicates the count of platelets obtained by measurement in the second measuring part 2.

A judgement equation (1) is used to check the reliability of PLT-I, and a judgement equation (2) is used to check the reliability of PLT-O. These judgement equations will be described with reference to FIGS. 3A, 3B, 4A and 4B.

An area which is adjacent to a platelet clustering area in the distribution diagram and in which particles do not appear in normal measurement, is set, and the judgement is made by means of a frequency of appearance (hereinafter referred to as a "frequency") of particles in the area. According to the judgement equation (1), the frequency on a division line "a" of FIG. 3A, the frequency on division lines "b" and "c" of FIG. 3B, and the frequency in an area "d" of FIG. 4A are checked, and when the frequency becomes a fixed value or greater (division line a: $RL \geq 5\%$, division line b: $PL \geq 15\%$, division line c: $PU \geq 25\%$, area $d \geq 500$), it is judged that the count of platelets obtained from the distribution diagram of FIG. 3B has low reliability. According to the judgement equation (2), the frequency in an area "e" of FIG. 4B is checked, and when the frequency becomes a fixed value or greater (area $e \geq 40$), it is judged that the count of platelets obtained from the distribution diagram of FIG. 4B has low reliability.

Figure 3A:
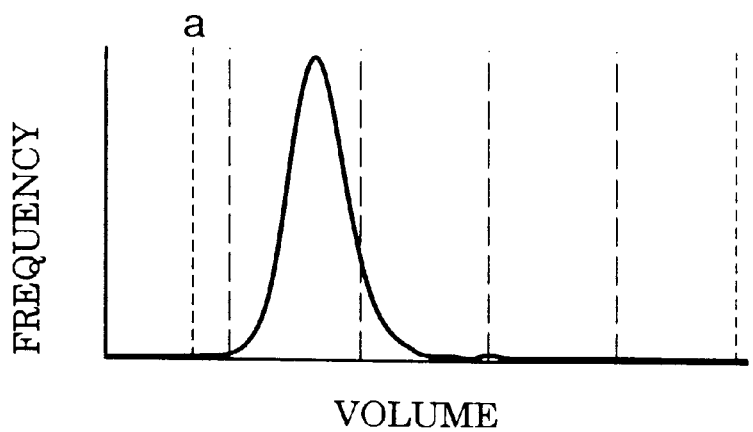
FIGS. 3A and 3B are diagrams showing measurement results when normal samples are measured in the embodiment of the present invention.
Figure 3B:
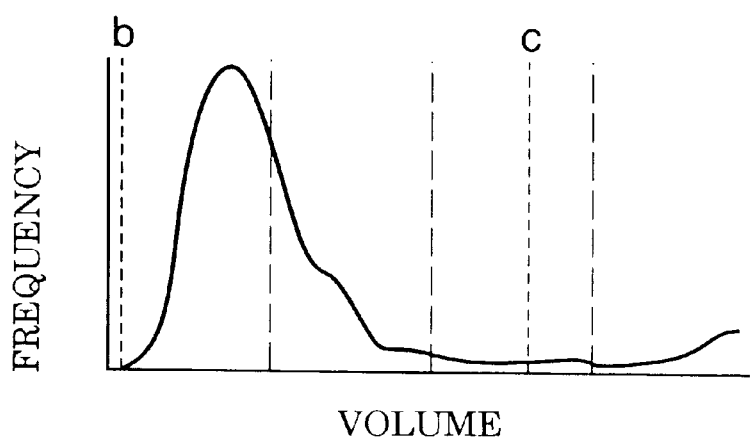
Figure 4A:
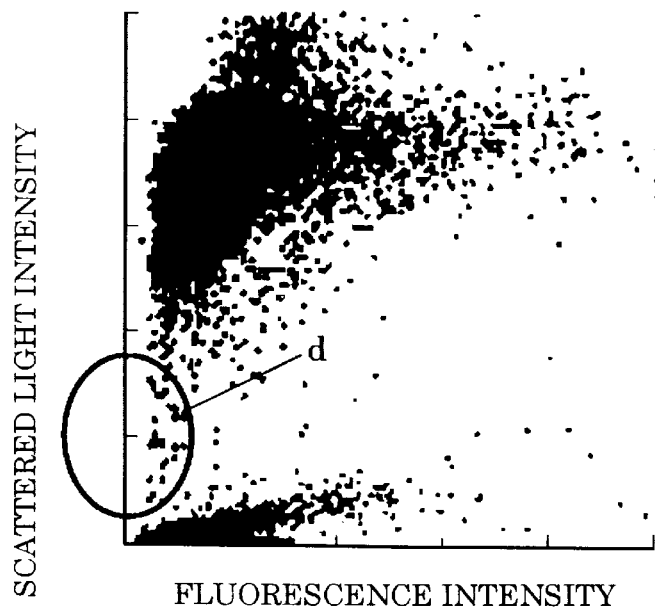
FIGS. 4A and 4B are diagrams showing measurement results when the normal samples are measured in the embodiment of the present invention.
Figure 4B:
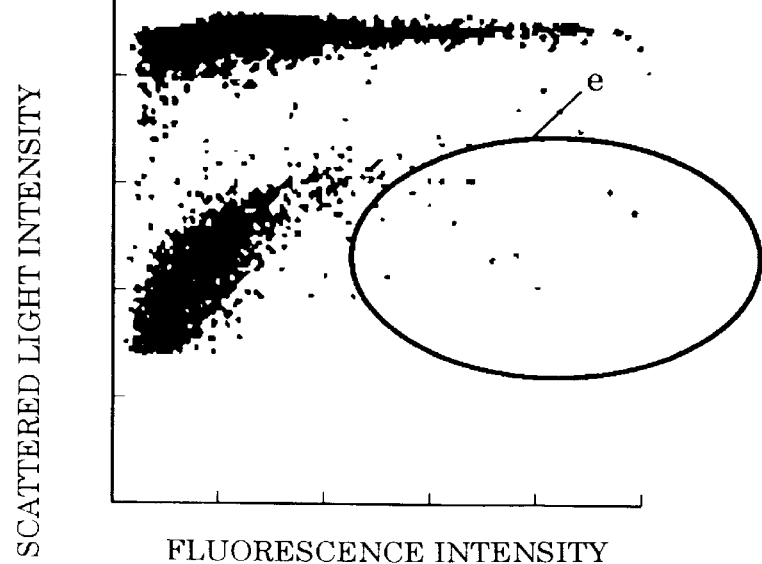

FIGS. 3A, 3B, 4A, and 4B are distribution diagrams when normal samples are measured. FIG. 3A is an erythrocyte histogram by measurement in the first measuring part 1, FIG. 3B is a platelet histogram by measurement in the first measuring part 1, FIG. 4A is a fluorescence intensity—scattered light intensity (linear) scattergram by measurement in the second measuring part 2, and FIG. 4B is a fluorescence intensity—scattered light intensity (log) scattergram by measurement in the second measuring part 2.

Here, on the basis of the judgement equation (1), since the frequency on the division line "a" of FIG. 3A, the frequencies on the division lines "b" and "c" of FIG. 3B, and the frequency in the area "d" of FIG. 4A are low (RL=2%, PL=3%, PU=7%, d=17), it is judged that the reliability of PLT-I is high, and the count of platelets of PLT-I is outputted. Here, although the judgement equation (2) is not applied, when the scattergram of FIG. 4B is checked, the frequency of the area "e" is low (e=12), and it is understood that the reliability of PLT-O is high. At this time, the count of platelets (PLT-I) was $24.1 \times 10^4/\mu l$. On the other hand, the count of platelets (PLT-O) was $25.0 \times 10^4/\mu l$ which was comparable to PLT-I.

Here, both of the division lines "a" and "c" are lines for differentiating the platelets from the erythrocytes (left side of each of the lines indicates the platelets), and when there are fragment erythrocytes, micro erythrocytes, giant platelets, or the like, the frequency on the division line becomes high. Thus, accurate differentiation from the platelets becomes impossible, and the reliability of PLT-I becomes low. The division line "b" is a line for differentiating noises from the platelets (right side indicates the platelets), and when there are fragment erythrocytes, electrical noises, bubbles or the like, the frequency on the division line becomes high. Thus, accurate differentiation from the platelets becomes impossible, and the reliability of PLT-I becomes low. In the area "d", when there are fragment erythrocytes, micro erythrocytes, or the like, the frequency on the area becomes high, which has the same meaning as the case where the frequency of the division line "a" or "c" becomes high, and the reliability of PLT-I becomes low. In the area "e", when there are fragment leukocytes or the like, the frequency of the area becomes high. Thus, accurate differentiation from the platelets becomes impossible, and the reliability of PLT-O becomes low.

A blood cell group appearing on the scattergram will be described with reference to FIGS. 4A and 4B. In FIGS. 4A and 4B, the blood cell group is roughly divided into two group areas. The upper group area indicates erythrocytes, and the lower group area indicates platelets. Further, the upper erythrocyte group area is divided into mature erythrocytes and reticulocytes, and the group area having high fluorescence intensity is reticulocytes.

Figure 5A:
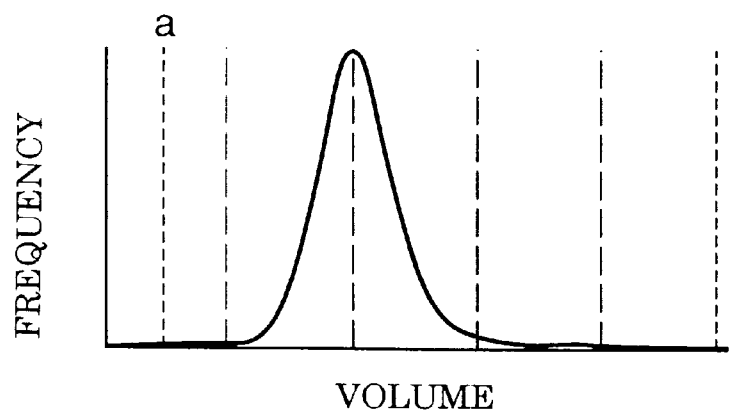
FIGS. 5A and 5B are diagrams showing measurement results when abnormal samples are measured in the embodiment of the present invention.
Figure 5B:
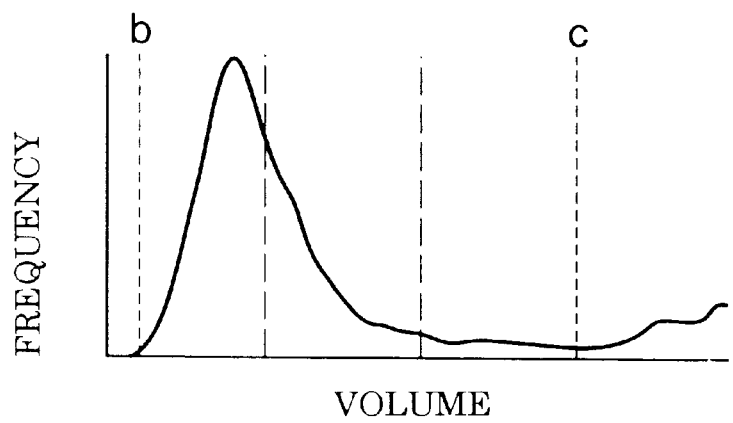
Figure 6A:
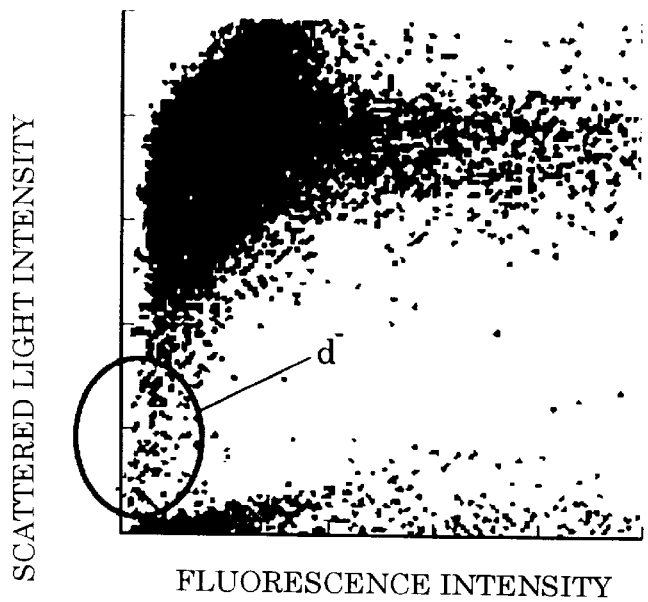
FIGS. 6A and 6B are diagrams showing measurement results when the abnormal samples are measured in the embodiment of the present invention.
Figure 6B:
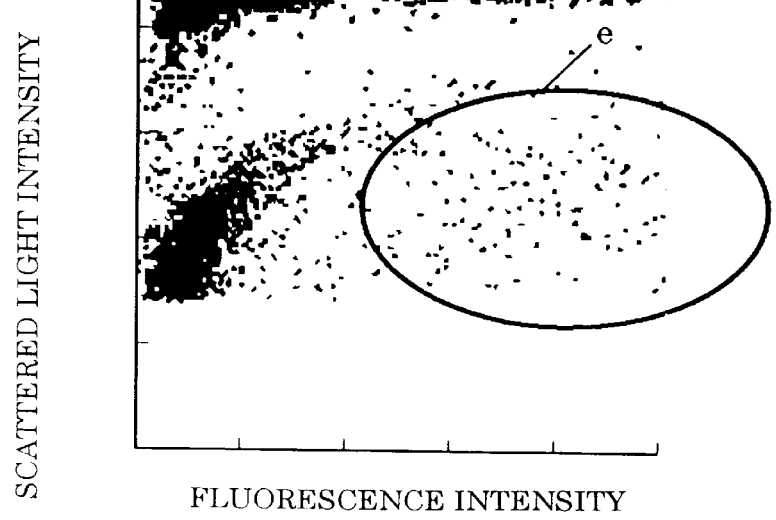

FIGS. 5A, 5B, 6A, and 6B are distribution diagrams obtained when abnormal samples including fragment leukocytes, or the like are measured. FIG. 5A is an erythrocyte histogram by measurement in the first measuring part, FIG. 5B is a platelet histogram by measurement in the first measuring part, FIG. 6A is a fluorescence intensity—scattered light intensity (linear) scattergram by measurement in the second measuring part, and FIG. 6B is a fluorescence intensity—scattered light intensity (log) scattergram by measurement in the second measuring part.

Here, on the basis of the judgement equation (1), since the frequency on the division line "a" of FIG. 5A, the frequencies on the division lines "b" and "c" of FIG. 5B, and the frequency of the area "d" of FIG. 6A are low (RL=1%, PL=5%, PU=8%, d=57), it is judged that the reliability of PLT-I is high, and the count of platelets of PLT-I is outputted. Here, although the judgement equation (2) is not applied, when the scattergram of FIG. 6B is checked, it is understood that the frequency of the area "e" is high (e=51) and the reliability of PLT-O is low. At this time, the count of platelets (PLT-I) was $7.8 \times 10^4/\mu l$. On the other hand, the count of platelets (PLT-O) was $29.4 \times 10^4/\mu l$. That is, the fragment leukocytes are overlapped in the platelet clustering area, so that the count of platelets becomes high.

Like this, even in the case where the fragment leukocytes or the like exist and the reliability of PLT-O is low, it is possible to output the count of platelets of PLT-I with high reliability.

Figure 7A:
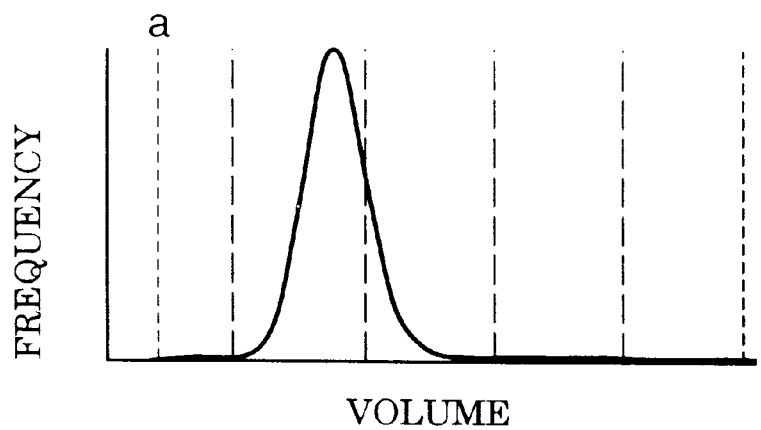
FIGS. 7A and 7B are diagrams showing measurement results when abnormal samples are measured in the embodiment of the present invention.
Figure 7B:
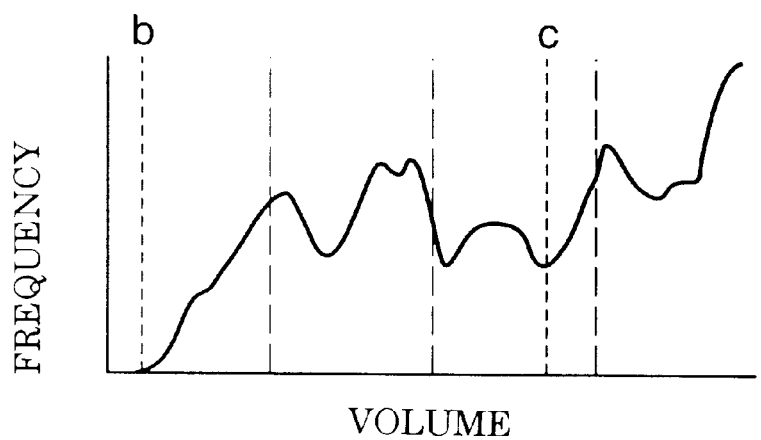
Figure 8A:
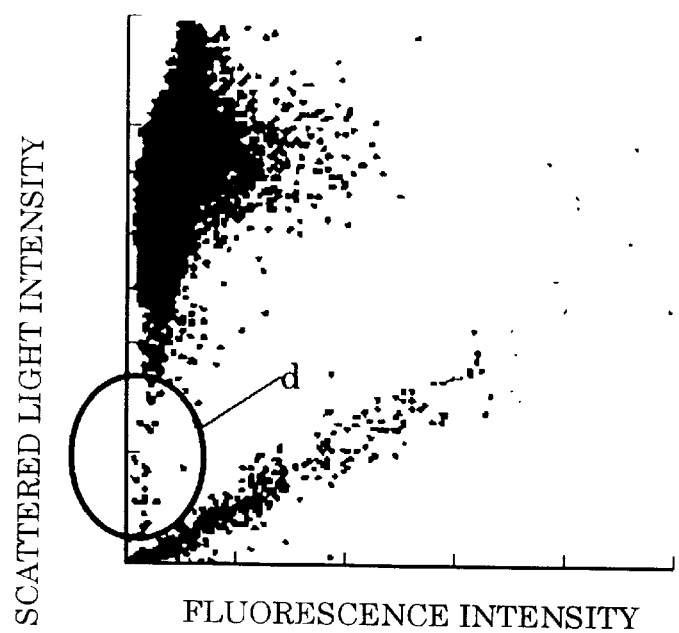
FIGS. 8A and 8B are diagrams showing measurement results when the abnormal samples are measured in the embodiment of the present invention.
Figure 8B:
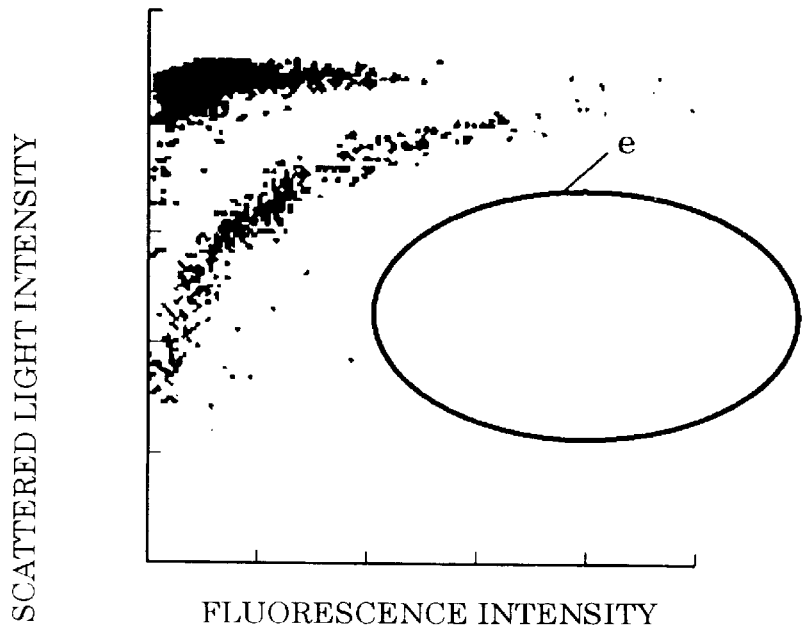

FIGS. 7A, 7B, 8A, and 8B are distribution diagrams obtained when abnormal samples containing giant platelets, or the like are measured. FIG. 7A is an erythrocyte histogram by measurement in the first measuring part, FIG. 7B is a platelet histogram by measurement in the first measuring part, FIG. 8A is a fluorescence intensity—scattered light intensity (linear) scattergram by measurement in the second measuring part, and FIG. 8B is a fluorescence intensity—scattered light intensity (log) scattergram by measurement in the second measuring part.

Here, on the basis of the judgement equation (1), since the frequency on the division line "c" of FIG. 7B is high (RL=4%, PL=2%, PU=40%, d=20), it is judged that the reliability of PLT-I is low. Next, on the basis of the judgement equation (2), since the frequency of the area "e" of FIG. 8B is low (e=0), it is judged that the reliability of PLT-O is high, and the count of platelets of PLT-O is outputted. At this time, the count of platelets (PLT-O) was $2.8 \times 10^4/\mu l$. On the other hand, the count of platelets (PLT-I) was $1.8 \times 10^4/\mu l$. That is, differentiation between platelets and erythrocytes cannot be accurately made due to existence of the giant platelets, and the giant platelets are removed from the platelet clustering area, so that the count of platelets becomes low.

Like this, even in the case where the giant platelets or the like exist and the reliability of PLT-I is low, it is possible to output the count of platelets of PLT-O with high reliability.

Figure 9A:
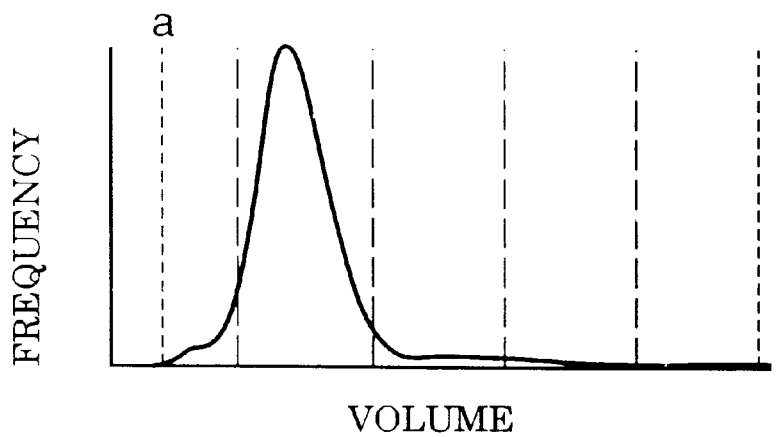
FIGS. 9A and 9B are diagrams showing measurement results when abnormal samples are measured in the embodiment of the present invention.
Figure 9B:
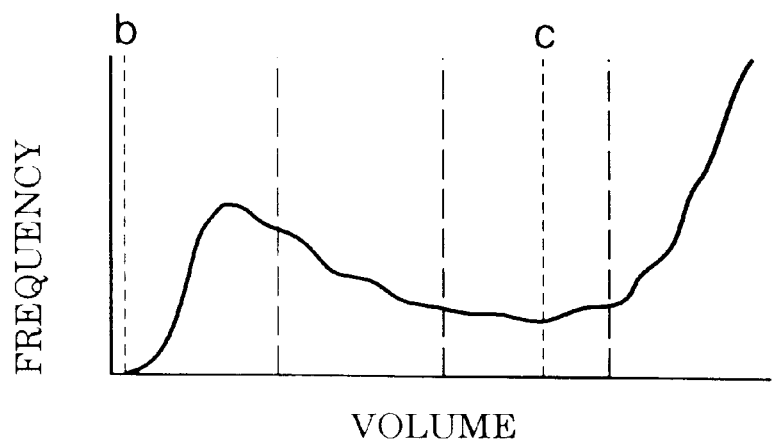
Figure 10A:
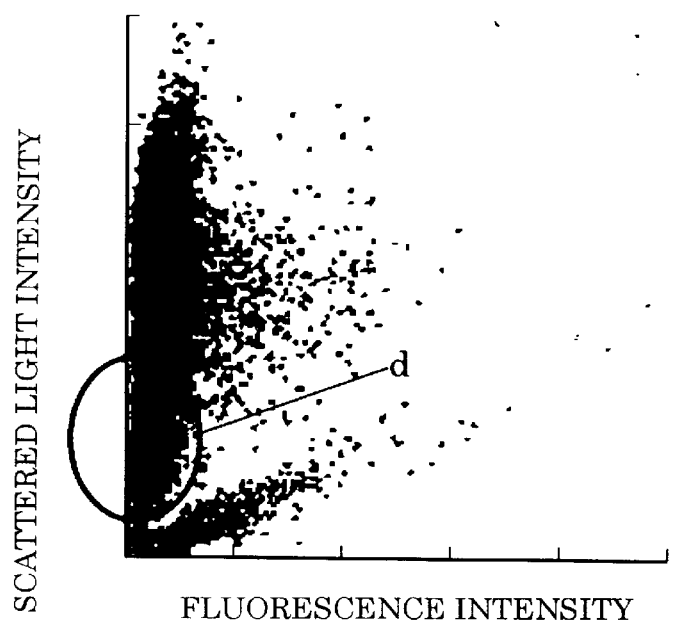
FIGS. 10A and 10B are diagrams showing measurement results when abnormal samples are measured in the embodiment of the present invention.
Figure 10B:
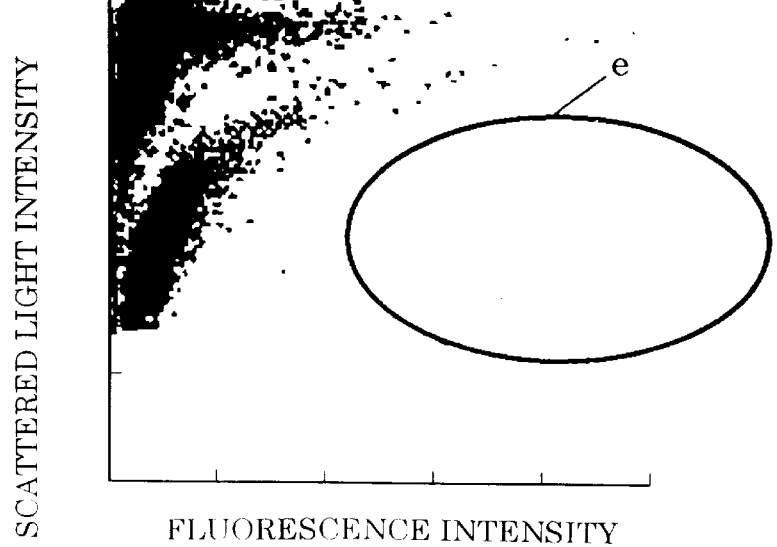

FIGS. 9A, 9B, 10A, and 10B are distribution diagrams obtained when abnormal samples containing fragment erythrocytes, or the like are measured. FIG. 9A is an erythrocyte histogram by measurement in the first measuring part, FIG. 9B is a platelet histogram by measurement in the first measuring part, FIG. 10A is a fluorescence intensity—scattered light intensity (linear) scattergram by measurement in the second measuring part, and FIG. 10B is a fluorescence intensity—scattered light intensity (log) scattergram by measurement in the second measuring part.

Here, on the basis of the judgement equation (1), since the frequency on the division line "c" of FIG. 9B is high and the frequency in the area d of FIG. 10A is high (RL=3%, PL=1%, PU=26%, d=2400), it is judged that the reliability of PLT-I is low. Next, on the basis of the judgement equation (2), since the frequency in the area "e" of FIG. 10B is low (e=1), it is judged that the reliability of PLT-I is high, and the count of platelets of PLT-O is outputted. At this time, the count of platelets (PLT-O) was $26.4 \times 10^4/\mu l$. On the other hand, the count of platelets (PLT-I) was $35.5 \times 10^4/\mu l$. That is, differentiation between platelets and erythrocytes cannot be accurately made due to existence of the fragment erythrocytes, and the fragment erythrocytes are overlapped to the platelet clustering area, so that the count of platelets becomes high.

Like this, even in the case where the fragment erythrocytes or the like exist and the reliability of PLT-I is low, it is possible to output the count of platelets of PLT-O with high reliability.

As described above, by using the two different measurement principles and judging and outputting data with high reliability according to either one of the principles, irrespective of normal samples or abnormal samples, it is possible to complement each other even for a sample with low reliability according to a measurement principle, so that it is possible to output the count of platelets with high reliability and high accuracy.

Although the description has been made on the case where measurement is made by using a plurality of measurement principles and either one of measurement results having high reliability is outputted, a description will be made on a case where measurement is made by using at least one measurement principle and after judgement of the reliability of the measurement result, an action message to urge measurement with another measurement principle is outputted.

Figure 13:
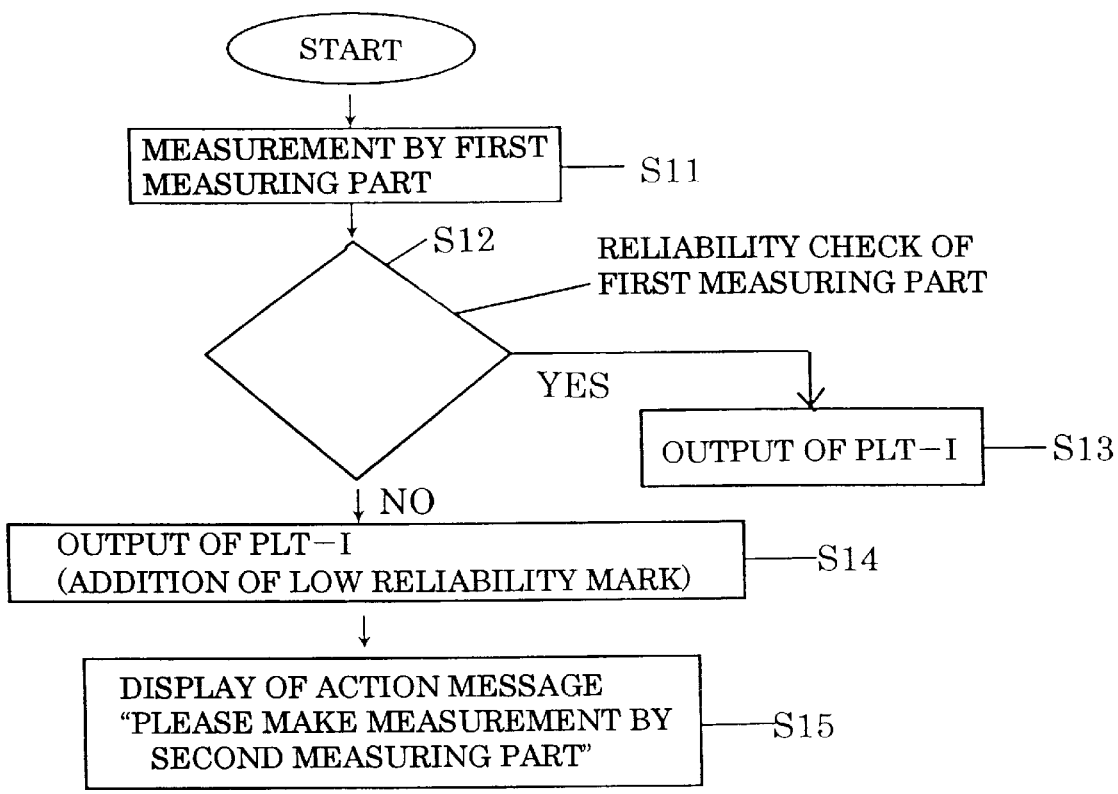
FIG. 13 is a measurement flowchart of another embodiment of the present invention.

With reference to a flowchart shown in FIG. 13, a description will be made on a procedure up to a stage in which measurement for the count of platelets is made by at least one measurement principle and a measurement result with high reliability is outputted.

First, measurement is made by the first measuring part (step S11), and the reliability of PLT-I is checked (step S12). In the case where the reliability is higher than a fixed value, the measurement result of PLT-I is outputted (step S13). In the case where the reliability of PLT-I is lower than the fixed value, in the output of PLT-I, the measurement result added with a low reliability mark is outputted (step S14). Next, an action message for urging measurement by the second measuring part is displayed (step S15).

Like this, even if measurement is not made by using a plurality of different measurement principles from the first, measurement is first made by at least one measurement principle, and the reliability of the measurement result is judged. Thereafter, in the case where it is necessary to make measurement by another measurement principle, an action message to urge the operator to make a next action is displayed, so that the reliability of measurement result can also be improved. In addition, since it is not always necessary to make measurement by a plurality of measurement principles, consumption of a reagent can be reduced, and there is also an advantageous side in cost.

The present invention has effects as described below.

According to the present invention, a particle analyzing apparatus comprises a plurality of different measuring parts for measuring a measurement item of a particle to be analyzed by means of a plurality of different measurement principles; a judgement processing part connected to these measuring parts and for making judgement processing of measurement results in the respective measuring parts on the basis of a plurality of predetermined reliabilities; and an output part connected to the judgement processing part and for outputting the measurement result on the basis of any one reliability in the judgement processing part. Thus, by using the plurality of different measurement principles and judging and outputting data with high reliability according to any one of the principles, irrespective of normal samples or abnormal samples, it is possible to complement each other even for a sample with low reliability according to a measurement principle, so that it becomes possible to output the measurement result with high reliability and high accuracy.

What is claimed is:

1. A particle analyzing apparatus, comprising:
   a first measuring part for measuring a specific measurement item of a particle to be analyzed by a first measurement principle;
   a second measuring part for measuring the specific measurement item by a second measurement principle;
   a judgment processing part for determining reliability of the measurement item measured by the first measuring part and determining reliability of the measurement item measured by the second measuring part only when the measurement result in the first measuring part is determined to be unreliable; and
   an output part for outputting the measurement item measured by the first measuring part when the first measuring principle is determined to be reliable and outputting the measurement item measured by the second measuring part when the second measuring principle is determined to be reliable.

2. A particle analyzing apparatus according to claim 1, wherein the judgment processing part further sets an area adjacent to a distribution area of the particle to be analyzed in a distribution diagram obtained as a result of measurement in one of the first measuring part and the second measuring part and in which particles do not normally appear, and the reliability is a frequency of appearance of particles in the area.

3. A particle analyzing apparatus according to claim 1, wherein the particle to be analyzed is a blood cell component particle such as a platelet, leukocyte or erythrocyte.

4. A particle analyzing apparatus according to claim 1, wherein the measurement item is an item as to the count or size of blood cell component particles such as platelets, leukocytes or erythrocytes.

5. A particle analyzing apparatus according to claim 1, wherein the particle to be analyzed is a cell in urine, a cultured cell, or a microorganism.

6. A particle analyzing apparatus according to claim 1, wherein the measurement item is the count or size of cells in urine, cultured cells, or microorganisms.

7. A particle analyzing apparatus according to claim 1, wherein the first measurement principle is based on an electrical detection system that detects an electrical change generated when the particle passes through a detection zone, and the second measurement principle is based on an optical detection system that detects an optical change generated when the particle passes through a detection zone.

8. A particle analyzing apparatus according to claim 1, wherein the first measuring part is based on an impedance system that detects an electrical change generated when the particle passes through a detection zone, and the second measuring part is based on a flow cytometory system that detects an optical change generated when the particle passes through a detection zone.

9. A particle analyzing apparatus, comprising:

a first measuring part for measuring a specific measurement item of a particle to be analyzed by a first measurement principle;

a second measuring part for measuring the specific measurement item by a second measurement principle;

a judgment processing part for determining reliability of the measurement item measured by the first measuring part and for determining reliability of the measurement item measured by the second measuring part; and an output part for outputting the measurement item having a higher reliability.

10. A particle analyzing apparatus, comprising:

a first measuring part for measuring a specific measurement item of a particle to be analyzed by a first measurement principle;

a second measuring part for measuring the specific measurement item by a second measurement principle;

a judgment processing part for determining reliability of only the measurement item measured by the first measuring part; and an output part for outputting the measurement item measured by the first measuring part, the output part also outputting a message to urge measurement using the second measuring part when the reliability of the measurement item measured by the first measuring part is determined to be unreliable.

* * * * *